US00PP35298P2

(12) United States Plant Patent
Posey

(10) Patent No.: US PP35,298 P2
(45) Date of Patent: Aug. 8, 2023

(54) BOXWOOD PLANT NAMED 'BSPSN'

(50) Latin Name: *Buxus sempervirens*
Varietal Denomination: BSPSN

(71) Applicant: Posey & Son Nursery, LLC, Hazel Green, AL (US)

(72) Inventor: Jeffery Posey, Hazel Green, AL (US)

(73) Assignee: POSEY & SON NURSERY, LLC, Hazel Green, AL (US)

( * ) Notice: Subject to any disclaimer, the term of this patent is extended or adjusted under 35 U.S.C. 154(b) by 0 days.

(21) Appl. No.: 17/803,455

(22) Filed: Jul. 15, 2022

(51) Int. Cl.
*A01H 6/00* (2018.01)
*A01H 5/00* (2018.01)

(52) U.S. Cl.
USPC ..... Plt./226

(58) Field of Classification Search
USPC ..... Plt./226
CPC ..... A01H 6/00; A01H 5/00
See application file for complete search history.

*Primary Examiner* — Keith O. Robinson
(74) *Attorney, Agent, or Firm* — Nicholas J. Landau; Maynard Nexsen PC

(57) ABSTRACT

A new and distinct boxwood plant of unknown parentage is provided that originated as a chance seedling and/or mutation while growing in a grouping of 3000 *Buxus sempervirens* liners originally planted in March 1992 near Hazel Green, Ala. The new cultivar can be distinguished from other varieties of *Buxus sempervirens* in view of its balanced and dense growth habit that is maintained with little pruning, full and thick appearance, and large dark green foliage. It appears to resist leaf miner infestation, even when adjacent plants of other varieties are infested. It is well suited for outdoor ornamental use under conditions similar to those in Northern Alabama.

4 Drawing Sheets

Botanical classification: *Buxus sempervirens*.
Variety denomination: BSPSN.

BACKGROUND

The present disclosure relates to a new and distinct cultivar of *Buxus sempervirens* and will be referred to hereafter by its cultivar name, 'BSPSN'. 'BSPSN' is a new cultivar of boxwood grown for use as an ornamental plant. The Inventor discovered the new cultivar circa 1999 as a new and unique plant in a grouping of 3000 *Buxus sempervirens* liners originally planted in March 1992 near Hazel Green, Ala. It is presumed that the new cultivar arose as a spontaneous mutant. The unique plant was observed to develop foliage that was distinctly different in shape and color from those around it. Asexual propagation of the new cultivar was first accomplished by directly placing vegetative stem cuttings into concrete sand without rooting hormones outdoors. After propagation, the new cultivar was observed to have a different growth habit as compared to the other plants. Asexual propagation of the new cultivar by cuttings has determined that the characteristics are stable and are reproduced true to type in successive generations.

SUMMARY

The following traits have been repeatedly observed and represent the characteristics of the new cultivar. These attributes in combination distinguish 'BSPSN' as a unique cultivar of boxwood. Its form is balanced in the ratio of height and width. Its foliage denser and its habit more compact than other varieties of which we are aware. Its leaves are large and of a darker green than other varieties.

The two varieties most similar to 'BSPSN' are believed to be 'Vardar Valley' and 'Dee Runk'.

'Vardar Valley' is a dwarf mounding selection. 'BSPSN' differs from 'Vardar Valley' at least in that 'BSPSN' is taller and wider in habit—'BSPSN' typically matures 155 cm tall×155 cm wide, whereas 'Vardar Valley' matures 75 cm tall×135 cm wide. It is unknown whether 'Vardar Valley' is patented.

'Dee Runk' is a very upright selection. 'BSPSN' differs from 'Dee Runk' at least in that 'BSPSN' is shorter and wider in habit—'BSPSN' typically matures 155 cm tall×155 cm wide, whereas 'Dee Runk' matures 275 cm tall×75 cm wide. It is unknown whether 'Dee Runk' is patented.

BRIEF DESCRIPTION OF THE DRAWINGS

The accompanying color photographs illustrate the overall appearance and distinct characteristics of the new boxwood. The photographs were taken of twelve year-old offspring of the new variety in a field in Hazel Green, Ala.

The photograph in FIG. 1 provides a view of a specimen of 'BSPSN' showing its overall habit and branching, which is typical of the variety.

Figure 1:
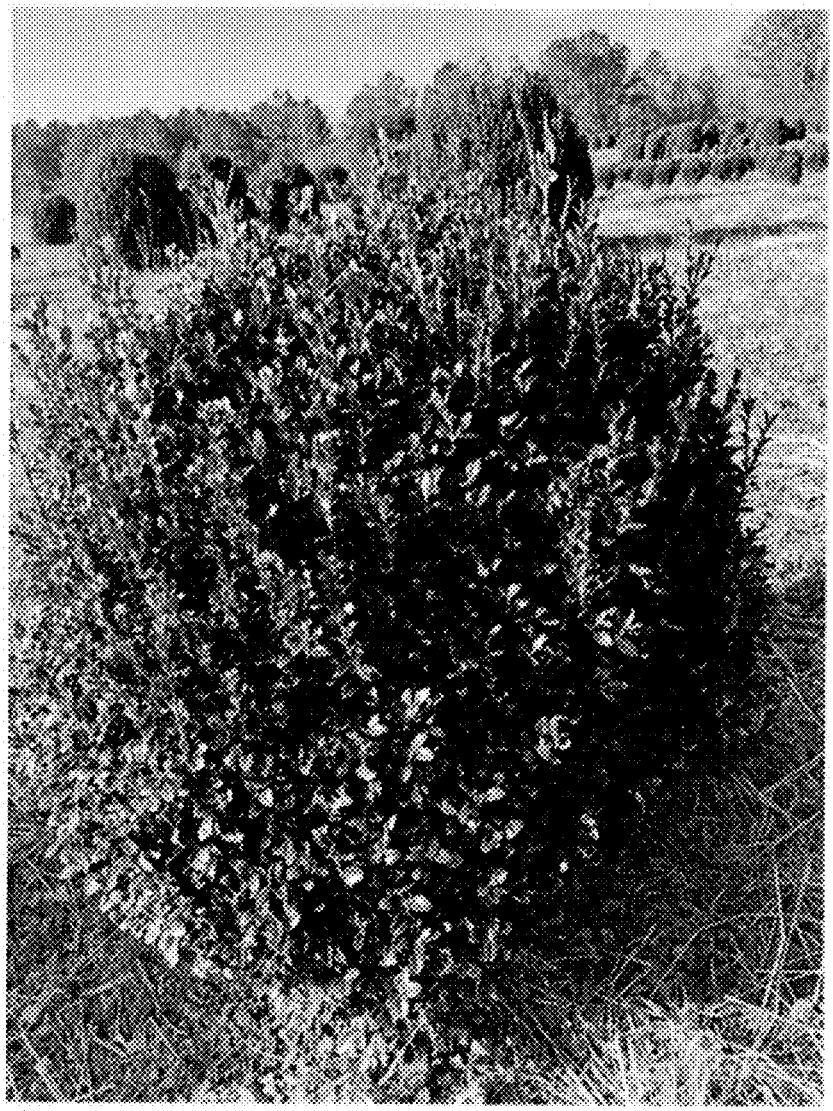
Figure 2:
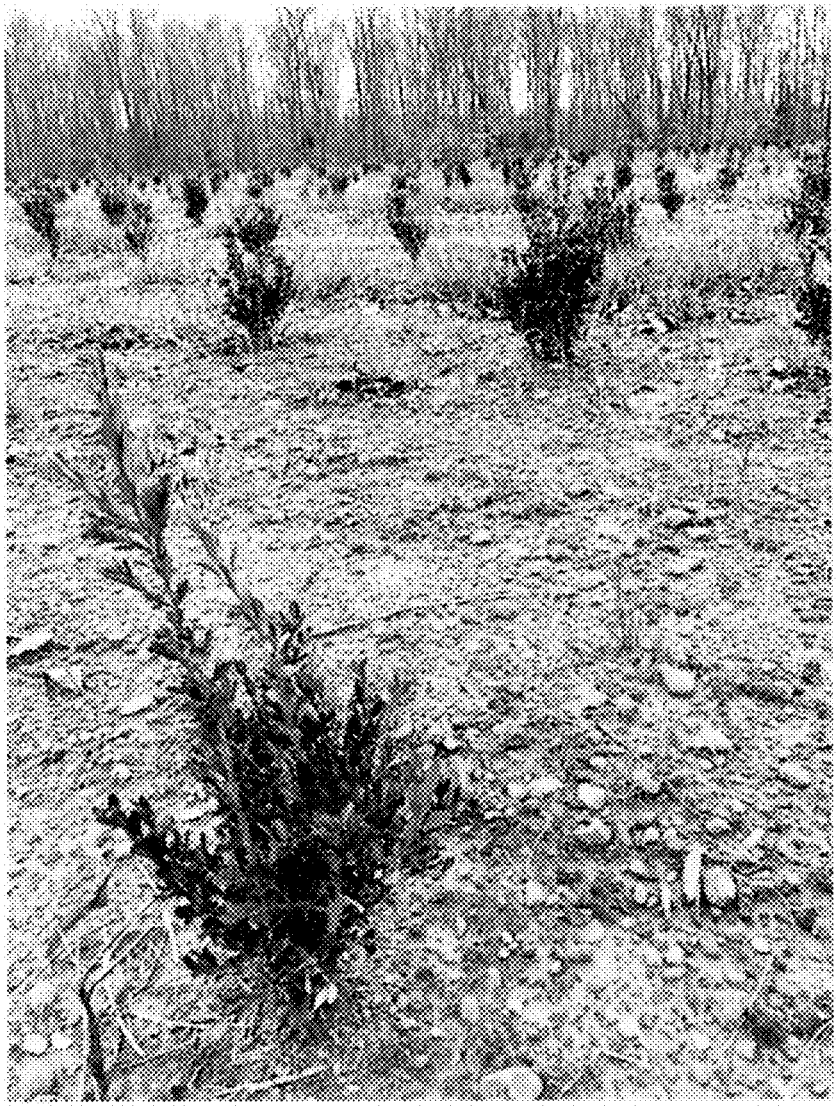

The photograph in FIG. 2 provides a view of a field of cultivated 'BSPSN' in the background, with a specimen of boxwood variety 'Green Mountain Boxwood' in the foreground for comparison.

Figure 3:
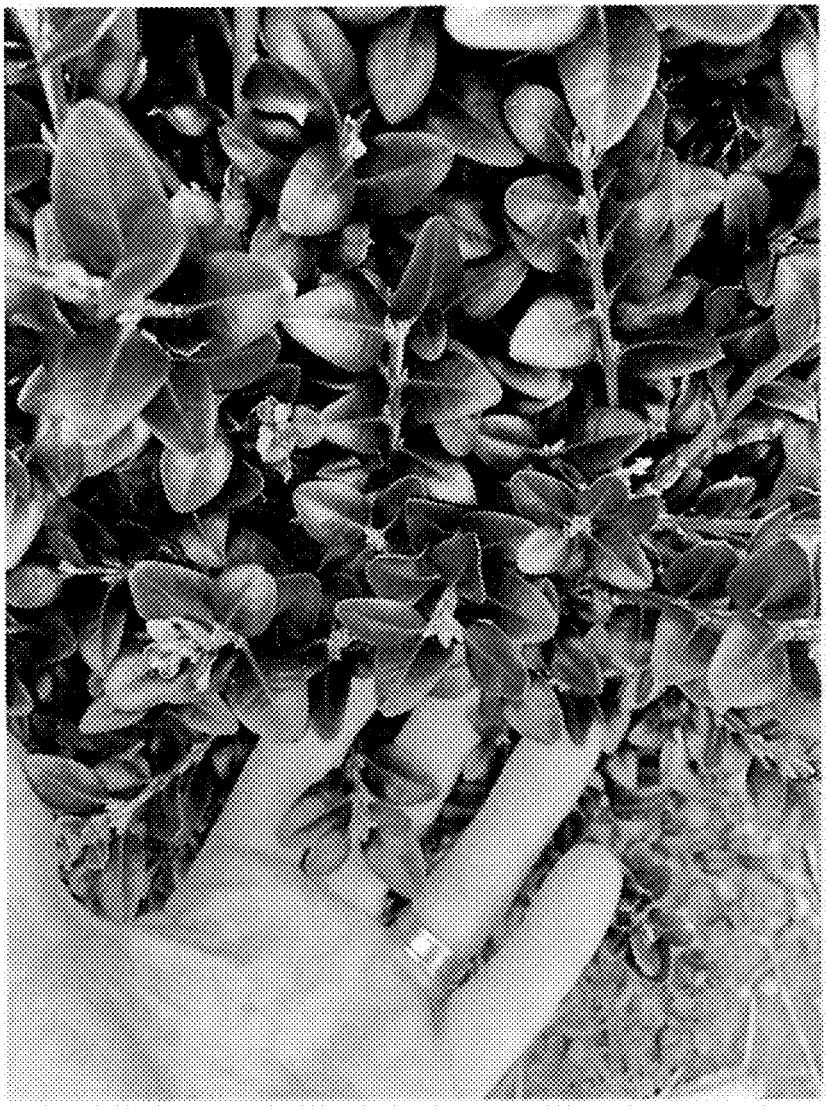

The photograph in FIG. 3 provides a detailed view of the foliage of 'BSPSN' taken in February of 2020.

Figure 4:
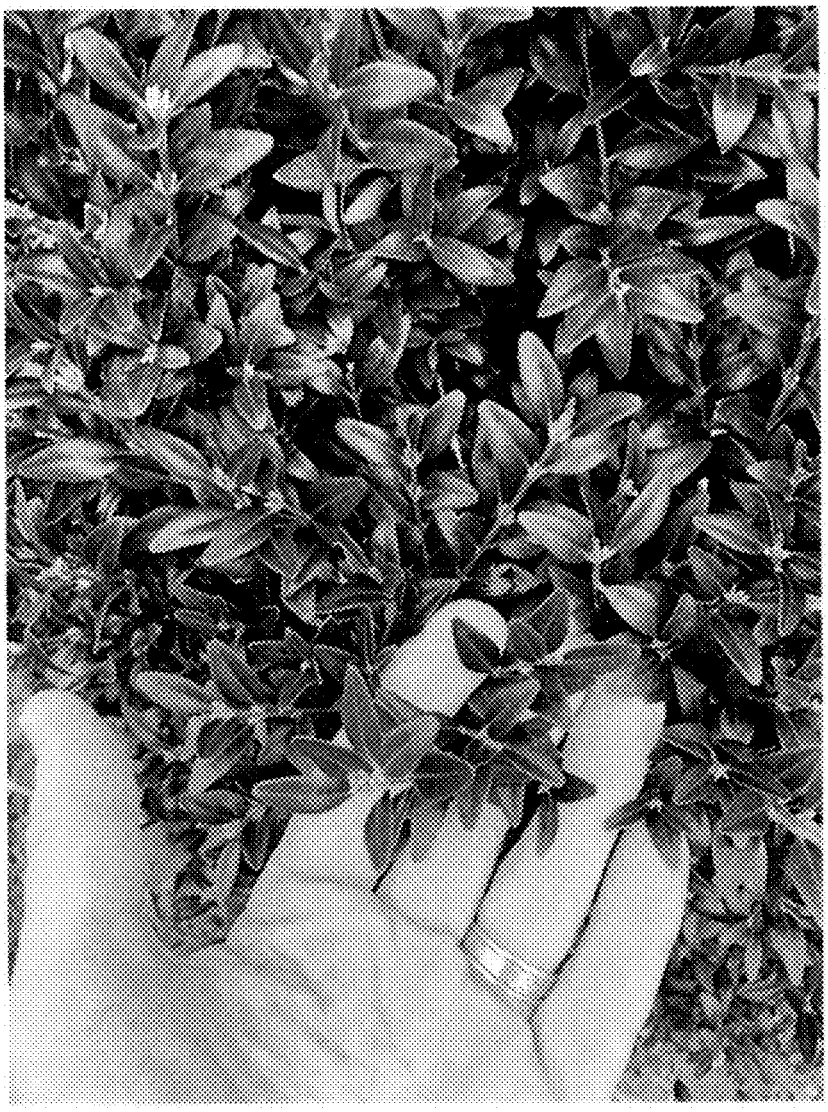

The photograph in FIG. 4 provides a detailed view of an unnamed or unknown boxwood variety grown under the same conditions as the specimen of 'BSPSN' shown in FIG. 3.

The colors in the photographs are as close as possible with the photographic and printing technology utilized and the color values cited in the detailed botanical description accurately describe the colors of the new boxwood.

DETAILED BOTANICAL DESCRIPTION

The following is a description of twelve-year-old plants of the new cultivar as grown under outdoor field production in Hazel Green, Ala. The phenotype of the new cultivar may vary with variations in environmental, climatic, and cultural conditions, as it has not been tested under all possible environmental conditions. The color determination is in accordance with *The* 2001 *Colour Chart of The Royal Horticultural Society*, London, England, except where general color terms of ordinary dictionary significance are used.

General description:

Species: *Buxus sempervirens.*

General type: Shrub.

Evergreen or deciduous? Evergreen.

Habit: Slightly upright rounded in youth to rounded at maturity.

Height and spread: 155 cm×155 cm at 20 years old.

Diseases resistances: Little to no issues with root rot (*Phytophthora* spp.) or canker (*Volutella buxi*) have been observed. The variety has not been fully evaluated for resistance to boxwood blight (*Calonectria pseudonaviculata*).

Pest resistances: Observed resistance to psyllids (*Psylla buxi*), mites (*Eurytetranychus buxi*) and scale (*Ceroplastes* spp.). This variety was not infested by leaf miners (*Monarthropalpus flavus*) when adjacent plots of other varieties of boxwood were infected with leaf miners.

Root description and color: Dense and fibrous; color: (new roots) White Group 155A, (mature roots) Greyed-Yellow Group 161A.

Propagation method: Vegetative cuttings taken in early March and stuck directly into concrete sand without rooting hormones. On average 80% of cuttings root out.

Root development timing: Root initials start to form in approximately 30 days.

Growth rate: Moderate; 9-10 cm per flush of growth.

Branch shape: Slightly fissured.

Branch color: (Softwood) Green Group 138A; (hardwood) mix of Greyed-Yellow Group 161C and Yellow-Green Group 147C.

Branch aspect: 55-60 degrees.

Branch size: (Softwood) 1 mm diameter; (hardwood $2^{nd}$ year growth) 5 mm diameter.

Branch strength: Thick and rigid; strong.

Branch surface: Slightly coarse.

Branch spacing: 3-5 cm on average.

Branching habit: Upright from base and decussate.

Internode length: 8 mm.

Leaf shape: New growth is ovate, becoming obovate during maturity.

Leaf division: Simple.

Leaf arrangement: Opposite.

Leaf base: Rounded to oblique.

Leaf aspect: 55-60 degrees.

Leaf apex: Obtuse.

Leaf venation coloration and shape: Mid-vein, Yellow-Green Group 147D.

Leaf margins: Entire.

Leaf surface: Upper surface is smooth and glossy; underside is smooth and matte.

Leaf size: Mature leaf is 18-20 mm long by 15-16 mm wide.

Leaf quantity: Average of 10 leaves per 5 cm.

Leaf color: Upper surface is Green Group 139A; underside is Yellow-Green Group 147B.

Petiole size, texture, color: 1-2 mm in length, smooth, Green Group 138A.

Inflorescence description: Occurs late March to early April in Hazel Green, Ala.; monoecious in dense auxiliary clusters.

USDA hardiness zone: Zones 5-8.

The following is claimed:

1. A new and distinct boxwood plant named 'BSPSN' substantially as illustrated and described.

* * * * *